United States Patent [19]
Bohmholdt et al.

[11] Patent Number: 5,087,739
[45] Date of Patent: Feb. 11, 1992

[54] CIRCULATION PROCESS FOR THE PRODUCTION OF ALIPHATIC AND CYCLOALIPHATIC DIISOCYANATES

[75] Inventors: Gerd Bohmholdt, Marl-Polsum; Josef Disteldorf, Marl; Peter Kirchner, Bochum; Hans-Werner Michalczak, Herne, all of Fed. Rep. of Germany

[73] Assignee: Huels Aktiengesellschaft, Marl, Fed. Rep. of Germany

[21] Appl. No.: 707,948

[22] Filed: May 28, 1991

Related U.S. Application Data

[63] Continuation of Ser. No. 386,223, Jul. 28, 1989, abandoned.

[30] Foreign Application Priority Data

Aug. 18, 1988 [DE] Fed. Rep. of Germany ....... 3828033

[51] Int. Cl.$^5$ ............................................ C07C 263/00
[52] U.S. Cl. ..................................... 560/345; 560/344
[58] Field of Search ................................ 560/344, 345

[56] References Cited

U.S. PATENT DOCUMENTS 4,388,246  6/1983  Sundermann et al. .............. 560/345
4,596,679  6/1986  Hellbach et al. .

FOREIGN PATENT DOCUMENTS 3314790  10/1984  Fed. Rep. of Germany ...... 560/345

Primary Examiner—Alan Siegel
Attorney, Agent, or Firm—Oblon, Spivak, McClelland, Maier & Neustadt

[57] ABSTRACT

A circulation process for the production of (cyclo)aliphatic diisocyanates, in which the biscarbamate is produced from diamines, by-products from the thermal cracking, urea, and alcohol in the presence of N-unsubstituted carbamates and dialkyl carbonates, and with separation of $NH_3$; the subsequent cracking of the biscarbamate is carried out in the liquid phase without solvent; the diisocyanate and alcohol are condensed; the diisocyanate is subjected to a purifying distillation; and a portion of the cracking reaction mixture is discharged with the by-products formed and recycled to the biscarbamate production step after prior reaction with the crude alcohol formed, effectively utilizes the by-products formed in the cracking step and is an industrially practical and economical process.

15 Claims, 1 Drawing Sheet

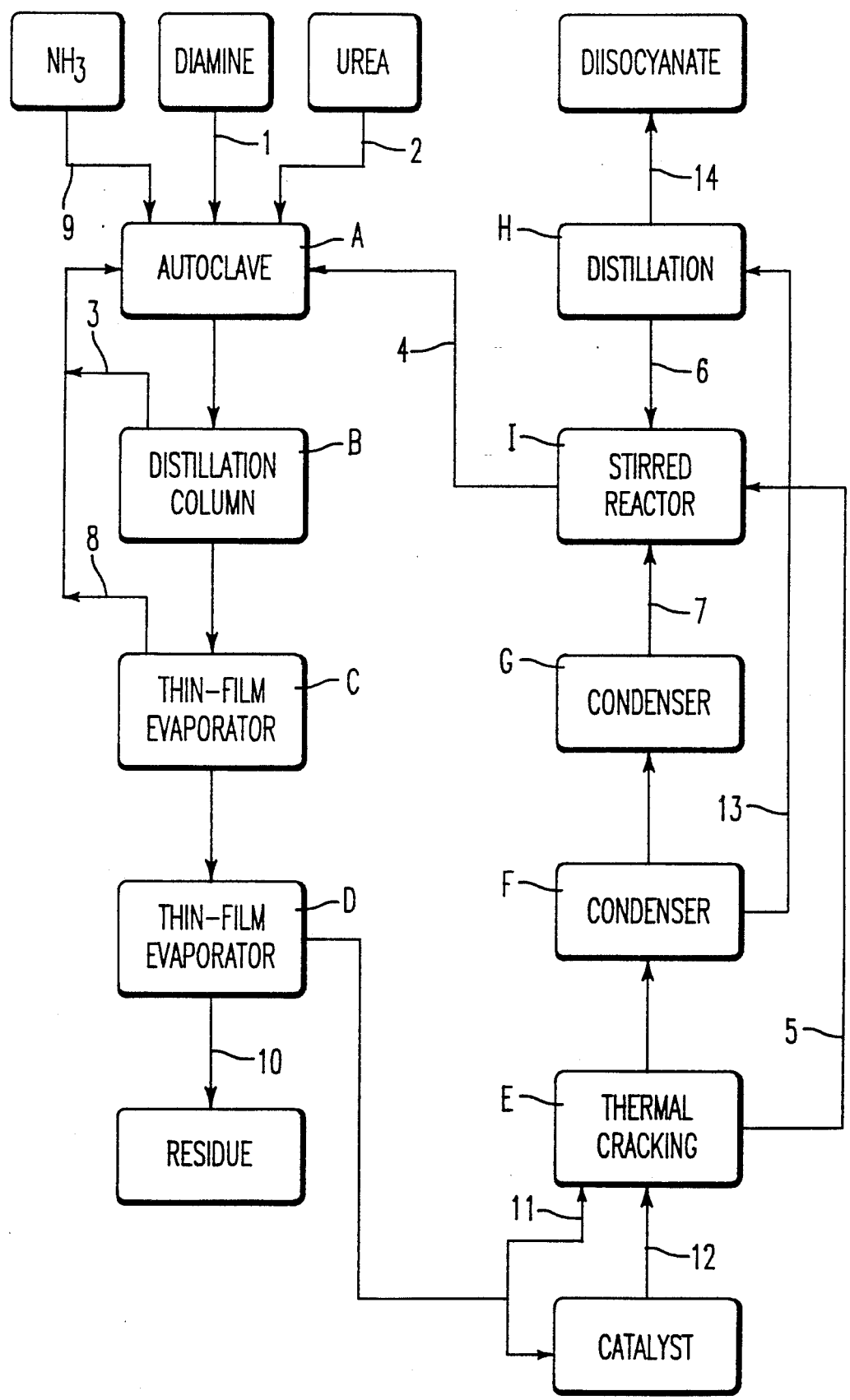

CIRCULATION PROCESS FOR THE PRODUCTION OF ALIPHATIC AND CYCLOALIPHATIC DIISOCYANATES

This application is a continuation of application Ser. No. 07/386,223, filed on July 28, 1989, now abandoned.

BACKGROUND OF THE INVENTION

1. Field of the Invention

The present invention relates to an improved process for the phosgene-free production of aliphatic and cycloaliphatic diisocyanates by the conversion of aliphatic and cycloaliphatic diamines into the corresponding biscarbamates and their continuous thermal cracking in the liquid phase without solvent, with the by-products formed during the cracking being discharged and recycled into the biscarbamate production process.

2. Discussion of the Background

One method for producing aliphatic and cycloaliphatic, hereinafter referred to as (cyclo)aliphatic, biscarbamates consists of the reaction of (cyclo)aliphatic diamines with urea and alcohols with the loss of ammonia, as described in European Patent 18 586. Other methods involve the complete or partial substitution of urea or diamines by compounds containing carbonyl groups, for example by N-unsubstituted carbamates and/or dialkyl carbonates, or mono- or disubstituted ureas or polyureas, such as those that also occur as intermediates in the above-mentioned reaction of diamines with urea and alcohols (cf. European Patents 27 952, 27 953, 28 331, and European Patent Application Disclosures 126 299 and 126 300).

The thermal cracking of (cyclo)aliphatic, and especially aromatic, mono- and biscarbamates into the corresponding isocyanates and alcohols has long been known, and can be carried out either in the gas phase at high temperatures or at relatively low temperatures in the liquid phase. However, it is a problem in both methods that unwanted side reactions also take place, in principle because of the thermal load. These side reactions not only reduce the yields, but also give rise to resinifying by-products that interfere substantially with the course of an industrial process by coating and plugging reactors and processing equipment.

Therefore, there has been no lack of suggestions for improving yields and reducing the formation of by-products by selective chemical and process steps. Thus, catalysts are described in DE-PS 1 022 222, DE-AS 19 44 719, U.S. Pat. No. 3,919,279, and DE-AS 26 35 490 which accelerate the cracking reaction of carbamates. The disclosed catalysts are a number of basic, acidic, and organometallic compounds, that do in fact substantially improve the yields of isocyanates in comparison with uncatalyzed reactions, but are not able to prevent the formation of by-products. The same also applies to the additional use of inert solvents, to provide for the most uniform possible distribution of the supplied heat and the catalyst in the reaction medium, as recommended also in U.S. Pat. No. 3,919,279 and DE-AS 26 35 490.

It is also disclosed in European Patent 54 817 that monocarbamates can be cracked in good yields without the use of solvents at relatively low temperatures, preferably at reduced pressure, optionally in the presence of catalysts and/or stabilizers, with the cracking products, isocyanate and alcohol, being removed by distillation, by boiling the reaction mixture, and being collected separately by fractional condensation. A partial discharge of the reaction mixture to separate the by-products formed during the cracking is also described in the examples listed. The possible utilization of these residues is not disclosed.

On the other hand, in European Patent 61 013, the thermal cracking of aromatic and (cyclo)aliphatic biscarbamates is carried out with the addition of catalysts and auxiliaries comparable to those described in European Patent 54 817, again in the presence of solvents. The solvents apparently also serve to absorb nonvolatile side products that are formed, which are then separated and discarded after discharge. However, use of refluxing solvents basically leads to a reduction of the space/time yields of the isocyanates and requires an additional expenditure of energy. No information is given concerning the extent of recovery of solvent. Furthermore, auxiliaries are used that are volatile under the reaction conditions and lead to contamination of the cracking products. The high proportion of residue compared to the diisocyanate formed is also particularly noticeable and, along with the low operating pressure, casts doubt on the suitability of this method as an economical and problem-free industrial procedure.

European Patent 92 738, in part, describes the thermal cracking of the cycloaliphatic biscarbamate 5-(ethoxycarbonylamino)-1-(ethoxycarbonylaminomethyl)-1,3,3-trimethylcyclohexane, which is fed along the inner wall of a tubular reactor in liquid form in the presence of a high-boiling solvent. Drawbacks of this process include the low yield (51.8%) and selectivity (91.9%) for the corresponding diisocyanate. Results of a continuous procedure with recycling of the recombined or partially cracked biscarbamate are not given, nor is information on the processing of the solvent containing the by-products and catalyst given.

In summary, it can be stated that in the cited publications, regardless of whether they refer only to the cracking of biscarbamates or also include their production, there are no references to a yield-improving utilization of the sometimes high proportions of residue formed during the cracking of the carbamate, which also lead to contamination of the distillate and plugging of the system components during the distillation, by decomposition and formation of resinous encrustations.

European Disclosure 133 274 describes the reaction of esters of N-substituted allophanic acids and/or polyallophanic acids with alcohols in the absence or presence of catalysts at temperatures of at least 160° C. to obtain carbamates. The allophanates in this case are exclusively those that can be formed by the reaction of compounds containing isocyanate groups with compounds containing urethane groups in the distillation bottoms of the purification distillation of the crude isocyanate formed during the carbamate cracking.

However, the by-products that are formed in the cracking reactor during the thermal cracking of, in particular, biscarbamates are a mixture of a number of substances consisting of, among others, substituted high molecular weight, undistillable compounds containing uretdione, isocyanurate, allophanate, urea, polyuret, or carbodiimide groups. This is also obvious from the fact that they can be reacted only incompletely with alcohols to obtain carbamates in small proportion, like the allophanates of European Disclosure 133 274.

Thus, there remains a need for a method to prepare (cyclo)aliphatic diisocyanates by the thermal cracking of the corresponding biscarbamates by an industrially practical, economical circulation process, in high yields which utilizes the by-products produced in the thermal cracking and avoids the problems of the by-products coating and plugging the process equipment.

SUMMARY OF THE INVENTION

Accordingly, one object of the present invention is to provide a novel process for the preparation of (cyclo)aliphatic diisocyanates by the thermal cracking of the corresponding biscarbamates which is industrially practical and proceeds with high yields.

It is another object of the present invention to provide a process for the preparation of (cyclo)aliphatic diisocyanates by the thermal cracking of the corresponding biscarbamates which provides for the recycling of the by-products formed during the cracking reaction.

It is another object of the present invention to provide a process for the preparation of (cyclo)aliphatic diisocyanates which avoids the problem of the by-products from the cracking reaction coating and plugging the process equipment.

These and other objects which will become apparent in the course of the following detailed description have been achieved by the inventors' discovery that the high molecular weight by-products formed in the thermal cracking of biscarbamates, which must be discharged from the reactor as continuously as possible to guarantee a problem-free and selective reaction, can be reconverted in large part to biscarbamates in the presence of diamines, urea, and alcohol. The remaining residue in the workup of the biscarbamates is relatively stable to heat and can be separated by distillation without problems.

Thus, the present invention is a circulation process for the production of (cyclo)aliphatic diisocyanates of the formula OCN—$R^1$—NCO, comprising: converting a diamine into a biscarbamate; and thermal cracking of the biscarbamates, to obtain a diisocyanate, in which:

(i) (cyclo)aliphatic diamines of the formula $H_2N$—$R^1$—$NH_2$ and by-products from the thermal cracking of the biscarbamates are reacted with urea and alcohols of the formula $R^2$—OH in the presence of N-unsubstituted carbamates and dialkyl carbonates to obtain biscarbamates of the formula $R^2$—O—CO—NH—$R^1$—NH—CO—$OR^2$ with the simultaneous separation of the ammonia formed, in which:

$R^1$ is a straight-chain or branched aliphatic hydrocarbon group with a total of 4 to 12 carbon atoms, or a substituted or unsubstituted cycloaliphatic hydrocarbon group with a total of 5 to 13 carbon atoms, $R^2$ is a group derived by removing the hydroxyl group from a primary aliphatic alcohol with 1 to 8 carbon atoms;

(ii) the biscarbamate obtained in the reaction described in (i) is separated by distillation from any unreacted alcohol, N-unsubstituted carbamate, and dialkyl carbonate, which are recycled into the reaction with the by-products of the cracking step, and from any unutilizable residue;

(iii) the continuous thermal cracking of the biscarbamates is carried out in the liquid phase, in the absence of solvent, in the presence of catalysts, with the reaction mixture boiling, and with fractionation of the vapors which contain diisocyanate and alcohol;

(iv) the diisocyanate and alcohol produced by the cracking step are fractionally condensed as crude products, and the crude diisocyanate is subjected to purifying distillation; and (v) a portion of the reaction mixture from the cracking step with the by-products formed is discharged continuously and is recycled into the biscarbamate formation reaction described in (i) after prior reaction with the crude alcohol that is formed.

BRIEF DESCRIPTION OF THE DRAWING

A more complete appreciation of the invention and many of the attendant advantages thereof will be readily obtained as the same become better understood by reference to the following detailed description when considered in connection with the accompanying drawing, wherein:

FIG. 1 is a block diagram illustrating an apparatus for carrying out one embodiment of the present process.

DETAILED DESCRIPTION OF THE PREFERRED EMBODIMENTS

To produce the biscarbamates according to (i), the diamine and the by-products from the thermal cracking, about 10 to 50 wt. % dissolved in biscarbamate, in an amount of 5 to 80 g of by-products per 1 mole of diamine, are reacted with urea and alcohol, with the diamine, urea, and alcohol being present in a molar ratio of 1 : 2.03 : 4.0 to 1 : 2.2 : 10, preferably 1 : 2.06 : 7 to 1 : 2.1 : 7, in the presence of N-unsubstituted carbamate and dialkyl carbonate in an amount of 1 to 10 mole % each, based on the diamine, at temperatures of 180° to 250° C., preferably 220° to 240° C., and pressures from 2 to 80 bar depending on the alcohol used, preferably 10 to 13 bar, for 3 to 20 hours, preferably 5 to 8 hours. The biscarbamates can be produced either in batches or continuously, for example in a reactor cascade.

Examples of diamines suitable for the present process include: aliphatic diamines, such as 1,4-butanediamine, 2-methyl-1,5-pentanediamine, 2-ethyl-1,4-butanediamine, 1,6-hexanediamine, mixtures of 2,2,4- and 2,4,4-trimethyl-1,6-hexanediamine, 1,8-octanediamine, 1,10-decanediamine, and 1,12-dodecanediamine; and cycloaliphatic diamines, such as 1,4-cyclohexanediamine, 2-methyl- and/or 4-methyl-1,3-cyclohexanediamine, 1,3- and/or 1,4-cyclohexanebis(methylamine), 4,4'-methylenebis(aminocyclohexane), 5-amino-1-aminomethyl-1,3,3-trimethylcyclohexane, and octahydro-4,7-methano-1H-indenebis(methylamine).

Particularly preferred are 2-methyl-1,5-pentanediamine (MPDA), mixtures of 2,2,4- and 2,4,4-trimethyl-1,6-hexanediamine (TMDA), and 5-amino-1,3,3-trimethylcyclohexanemethylamine (IPDA).

Suitable as alcohols are all primary aliphatic alcohols, which, on the one hand, have a sufficiently large difference in boiling point from the diisocyanate being produced, and which, on the other hand, permit distillation of the biscarbamate and condensation of the cracking products at operating pressures favorable for process engineering. Therefore, methanol, ethanol, propanol, butanol, isobutanol, pentanol, isopentanols, hexanol, isohexanols, and 2-ethylhexanol are suitable. Butanol is preferred.

The by-products used in the production of the biscarbamate according to (i) are high molecular weight, thermally unstable compounds formed in the thermal cracking of biscarbamates by secondary and side reactions that are unavoidable in practice, which are continuously discharged from the reactor in dissolved form with a portion of the reaction mixture. The reactor discharge, after reacting any free NCO groups with the crude alcohol produced in the process, is recycled into the biscarbamate production step described in (i) as a 25 to 50% alcoholic solution of by-products and biscarbamates in a weight ratio of 1 : 9 to 1 : 1.

The other starting materials for the biscarbamate production mentioned previously, N-unsubstituted carbamate and dialkyl carbonate, are intermediates that are formed in small proportions by the reaction of the alcohol with urea, separated as a forerun in the distillation of the biscarbamate, and recycled into the biscarbamate production step in an amount of 1 to 10 mole % each based on the diamine.

In addition to a sufficiently high temperature and reaction time, a prerequisite for the most quantitative possible conversion of diamine and by-products is the continuous and essentially complete removal of the ammonia formed, which is driven out of the reaction mixture by the alcohol boiling under reflux. The alcohol is condensed at a temperature above 60° C. to avoid deposits of N-unsubstituted carbamate and ammonium carbamate/carbonate in which the latter may occur in traces under some circumstances.

The biscarbamate is worked up according to step (ii) by distilling off the excess alcohol and then separating a forerun and the undistillable residue in thin-film evaporators under reduced pressure. The forerun which contains N-unsubstituted carbamate and dialkyl carbonate is recycled into the biscarbamate production process step (i), and the residue that cannot be further utilized is discarded.

The continuously operated thermal cracking of the biscarbamate into diisocyanate and alcohol according to step (iii) is carried out in a stirred reactor in the presence of catalysts, preferably under vacuum conditions and at a temperature at which the content of the reactor boils. The feed material that is not cracked or only partly cracked, biscarbamate and monoisocyanatomonocarbamate, flows back into the reactor after fractionation, while the diisocyanate and alcohol are fractionally distilled as crude products as described in (iv).

The by-products formed during the cracking are removed from the reactor by continuous discharge of a portion of the reaction mixture as described in (v), with the weight ratio of the reactor discharge to initial biscarbamate being 1 : 20 to 1 : 1.5, preferably 1 : 8 to 1 : 3. The amount of reaction mixture discharged, depending on the diisocyanate to be produced, is such that a sufficiently low steady-state concentration of by-product is maintained, which is necessary for a selective and trouble free reaction.

The crude diisocyanate is subjected to purification by distillation, and the distillation bottoms, containing essentially monoisocyanatomonocarbamate in addition to residual fractions of diisocyanate, together with the reactor discharge and the crude alcohol formed in the process which contains small amounts of biscarbamate, are recycled into the biscarbamate production process described in (i), after reaction of the free NCO groups.

The thermal cracking of the biscarbamates is carried out in the presence of catalysts, especially compounds that have a catalytic effect on esterification reactions. Suitable catalysts include tertiary amines, Lewis acids, carboxylic acid salts, metal oxides, and organometallic compounds. In the selection of catalysts, care must be taken that they are thermally stable and nonvolatile under the particular reaction conditions, for reasons of product purity and constant cracking activity. Examples of catalysts that meet these requirements are: tris(-dodecyl)amine, tris(octadecyl)amine, ferrous chloride, cuprous chloride, zinc chloride, zinc bromide, zinc iodide, cadmium iodide, stannous chloride, stannous bromide, stannous iodide, stannic, zinc, ferric, cobalt, and manganese octanoate and naphthenate, cuprous oxide, stannic oxide, manganese dioxide, dibutyltin oxide, dibutyltin dilaurate, and titanium 2-ethylhexanoate. Especially preferred are zinc chloride, zinc bromide, zinc iodide, stannous chloride, stannous bromide, and stannous iodide.

The thermal cracking of the biscarbamate may be carried out at a temperature of 180° to 280° C., preferably 230° to 240° C., and at a pressure of 0.001 to 2 bar, preferably 0.005 to 0.05 bar.

The catalysts are suitably used in concentrations of 0.0001 to 10 wt. %, preferably 0.0005 to 0.05 wt. %, and particularly preferably 0.001 to 0.02 wt. %, based on the biscarbamate to be cracked.

Other features of the present invention will become apparent in the course of the following descriptions of exemplary embodiments which are given for illustration of the invention and are not intended to be limiting thereof.

EXAMPLES

The following Examples were carried out using an experimental apparatus illustrated in the block diagram given in FIG. 1, and the reference numerals and letters in the Examples refer to those in FIG. 1. Diamines and urea were fed into the closed process, and diisocyanates, ammonia, and residue were taken off with circulation of the other product streams. All percentages, if not otherwise noted, refer to percentages by weight.

EXAMPLE 1

(a) Preparation of 1,5-bis(butoxycarbonylamino)-2-methylpentane (MPDU) from MPDA, by-products of thermal cracking, urea, and butanol.

In one of two alternately operated oil-heated 25-liter stirred autoclaves followed by condensers, heated off-gas lines, and relief valves (A), 2,000 g of MPDA (1) and a solution (4) that had been produced by combining 1,740 g of reactor discharge (5) from the thermal cracking reactor (E) with approximately 30% by-products, 151 g of bottoms (6) from the MPDI purifying distillation (H), and 3,082 g of crude butanol (7) from the alcohol condensation (G), were heated to 230° C. over a period of approximately 2 h with 2,131 g of urea (2), 6,379 g of butanol (3), in an MPDA : urea : butanol molar ratio of 1 : 2.06 : 7, and 250 g of forerun (8) from the thin-film evaporator (C) for biscarbamate processing, which contained approximately equal portions of butyl carbamate and dibutyl carbonate along with residual amounts of butanol and MPDU, and the mixture was reacted for 5 h longer at this temperature. The ammonia (9) which was formed was released continuously when the pressure reached approximately 12 bar, with the butanol boiling under reflux. The condenser temperature was adjusted to 70° C. to avoid deposits of butyl carbamate and in some cases ammonium carbamate/carbonate.

After completion of the reaction, the butanol used in excess was distilled off in a column (B) operated continuously at 160° C. and 80 mbar, with 6,379 g of butanol (3) being obtained. In a thin-film evaporator (C), 250 g of a forerun (8) was then separated at 190° C. and 1 mbar, which could be used in the second autoclave for MPDU production (A) together with the butanol (3) driven off. The crude MPDU thus obtained was removed at 230° C. and 0.5 mbar in another thin-film evaporator (D) of the undistillable molten residue (10) that could no longer be converted into MPDU. The amount of MPDU distillate was 7,722 g, and the amount of residue was 148 g.

(b) Thermal cracking of MPDU into 1,5-diisocyanato-2-methylpentane (MPDI) and butanol The MPDU was cracked at 233° C. and 27 mbar in the presence of about 200 ppm of zinc chloride as catalyst in an oil-heated 750 ml stirred steel reactor equipped with a distillation column (E). This was loaded continuously with 598 g/h of MPDU (11) in molten form (80° C.) with a constant reactor content of 200 g through a metering device according to the available cracking capacity.

To separate the by-products formed, 174 g/h of the reactor contents was discharged (5), and to maintain this and the catalyst level, 174 g/h of MPDU (12) containing 200 ppm of zinc chloride was injected through another metering device.

The cracking occurred with intense boiling of the reaction mixture, with the escaping vapors going into a distillation column to separate the MPDU and monoisocyanatomonocarbamate from the vapors and return them back to the reactor.

The cracked MPDI and butanol were contained in the vapors and were condensed in two successive condensers (F, G) at 50° C. and 10° C., respectively. The crude MPDI (13) obtained, about 95% pure, was subjected to a purifying distillation (H), with 274.9 g/h of MPDI (14) having a purity of >99% and 15.1 g/h of bottoms (6) consisting essentially of monoisocyanatomonocarbamate being obtained. The 308 g/h of crude butanol (7) obtained with about 5% MPDU recombinate was collected in the stirred reactor (I) for the following MPDU production, together with the reactor discharge (5) and the distillation bottoms (6).

The 7,722 g of MPDU obtained from Example 1(a) with recycling of by-products corresponds to an interval of 10.0 hours when using 772 g/h of starting material with simultaneous discharge of a portion of the reaction mixture. From the 2,749 g of MPDI obtained during this time, the yield or selectivity of the overall process, based on the initial MPDA, is calculated to be 94.9%, which is also maintained for longer operating periods of the two steps (a) (intermittent) and (b) (continuous).

COMPARATIVE EXAMPLE 2

Thermal cracking of MPDU to MPDI and butanol with separation of by-products by distillation from the reactor discharge As described in Example 1(b), 772 g/h fed continuously into the cracking reactor for a period of 10 hours, and simultaneously, 174 g/h of the reactor content was discharged. After purifying the crude MPDI by distillation, 2,751 g of MPDI with a purity of >99% was obtained. The reactor discharge of 1,740 g and 151 g of bottoms from the purifying distillation, after reaction of the free NCO groups with 3,082 g of crude butanol, were distilled in a thin-film evaporator, by which 1,160 g of MPDU could be recovered. A cracking selectivity of 82.1% is calculated from this result. The remaining resinous residue could no longer be converted into MPDU.

COMPARATIVE EXAMPLE 3

Thermal cracking of MPDU into MPDI and butanol and thermal aftertreatment of the reactor discharge with butanol As described in Example 1(b), 772 g/h of MPDU was fed into the cracking reactor continuously over a period of 7.5 hours, and simultaneously, 174 g/h of the reactor content was discharged. After purifying the crude MPDI by distillation, 2,062 g of MPDI with a purity of >99% was obtained. The reactor discharge of 1,305 g and 113 g of bottoms from the purifying distillation were stirred for 5 hours at 230° C. with 2,310 g of crude butanol in an autoclave.

The subsequent processing by distillation in a thin-film evaporator provided 1,130 g of MPDU and, thus, an overall selectivity for cracking and aftertreatment of the by-products of 86.5%.

Note on Comparative Examples 2 and 3

In the separation of residues from thermal cracking by distillation with or without prior aftertreatment with alcohol (alcoholysis), process engineering problems resulted from the occurrence of caking and encrustation in the distillation equipment that could be removed only with difficulty. This difficulty was not observed in the process pursuant to the invention.

EXAMPLE 4

(a) Preparation of 5-(butoxycarbonylamino)-1-(butoxycarbonylaminomethyl)-1,3,3-trimethylcyclohexane (IPDU) from IPDA, by-products of thermal cracking, urea, and butanol By a procedure analogous to that described in Example 1(a), 3,400 g of IPDA (1) and a solution (4) that had been produced by combining 1,350 g of reactor discharge (5) from the thermal cracking (E) with approximately 40% by-products, 207 g of distillation bottoms (6) from the purifying distillation of IPDI (H), and 3,446 g of crude butanol (7) from the alcohol condensation (G), were reacted with 2,472 g of urea (2), 7,400 g of butanol (3), and 300 g of forerun (8) from the thin-film evaporator (C), with the IPDA : urea : butanol molar ratio being 1 : 2.06 : 7. After appropriate workup, 9,296 g of IPDU distillate and 146.5 g of residue (10) were obtained.

(b) Thermal cracking of IPDU into 5-isocyanato-1-(isocyanatomethyl)-1,3,3-trimethylcyclohexane (IPDI) and butanol The cracking was performed analogously to Example 1(b) at 235° C. and 27 mbar with continuous introduction of 795 g/h of IPDU (11) and 135 g/h of IPDU (12) containing 200 ppm of zinc chloride, and continuous discharge (5) of 135 g/h of the reactor contents.

The crude IPDI (13) was condensed at 50° C., and after a purifying distillation, provided 429.3 g/h of IPDI (14) with a purity of >99%. The 345 g/h of crude butanol (7) with about 5% IPDU recombinate obtained was collected in the stirred reactor (I) for the following IPDU production, together with the reactor discharge (5) and 20.7 g/h of distillation bottoms (6).

The 9,296 g of IPDU obtained from Example 4(a) with recycling of by-products corresponds to an interval of 10.0 hours when using 930 g/h of feed material in the cracking with simultaneous discharge of a portion of the reaction mixture. From the 4,293.5 g of IPDI obtained during this time, the yield or selectivity, based on the initial IPDA, of the overall process of 96.7% is calculated.

EXAMPLE 5

(a) Preparation of 1,6-bis(butoxycarbonylamino)-2,2,4(2,4,4)-trimethylhexane (TMDU) from TMDA, by-products of thermal cracking, urea, and butanol By a procedure analogous to that described in Example 1(a), 2,850 g of TMDA (1) and a solution (4) that had been produced by combining 1,900 g of reactor discharge (5) from the thermal cracking (E) with approximately 30% of by-products, 156 g of the distillation bottoms (6) from the purification of TMDI by distillation (H), and 3,173 g of crude butanol (7) from the alcohol condensation (G), were reacted with 2,229 g of urea (2), 6,674 g of butanol (3), and 300 g of forerun (8) from the thin-film evaporator (C), with the TMDA : urea : butanol molar ratio being 1 : 2.06 : 7. After appropriate workup, 8,873 g of TMDU distillate and 144 g of residue (10) were obtained.

(b) Thermal cracking of TMDU to 1,6-diisocyanato-2,2,4(2,4,4)-trimethylhexane (TMDI) and butanol The cracking was carried out analogously to Example 1(b) at 238° C. and 27 mbar with continuous introduction of 697 g/h of TMDU (11) and 190 g/h of TMDU (12) containing 10 ppm of stannous chloride, and with the continuous discharge (5) of 190 g/h of the reactor contents. The crude TMDI (13), condensed at 50° C, after purifying distillation, provided 364.4 g/h of TMDI (14) with a purity of >99%. The 317 g/h of crude butanol (7) obtained with about 5% TMDU recombinate was collected in the stirred reactor (I) together with the reactor discharge (5) and 15.6 g/h of distillation bottoms (6), for the following TMDU production. The 8,873 g of TMDU obtained from (a) with recycling of by-products corresponds to an interval of 10.0 hours when using 887 g/h of feed material in the cracking with simultaneous discharge of a portion of the reaction mixture. From the 3,644 g of TMDI obtained during this time, the yield or selectivity of the overall process of 96.2% is calculated, based on the initial TMDA.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing a (cyclo)aliphatic diisocyanate of the formula $$OCN-R^1-NCO$$

comprising the steps of: converting a (cyclo)aliphatic diamine of the formula $$H_2N-R'-NH_2$$

to a biscarbamate of the formula $$R^2-O-CO-NH-R^1-NH-CO-OR^2$$

and thermally cracking said biscarbamate, to obtain said diisocyanate, an alcohol of the formula $R^2OH$ and by-products, which comprises at least one compound selected from the group consisting of high molecular weight, undistillable compounds containing uretdione, isocyanurate, allophanate, urea, polyuret, or carbodiimide groups; wherein:

(i) said (cyclo)aliphatic diamine and said by-products are reacted with urea and said alcohol of the formula $R^2OH$ in the presence of N-unsubstituted carbamates and dialkyl carbonates with the simultaneous separation of any ammonia formed, to obtain a reaction mixture containing said biscarbamate, unreacted alcohol, N-unsubstituted carbamate, and dialkyl carbonate;

(ii) said biscarbamate obtained in (i) is separated from said unreacted alcohol, N-unsubstituted carbamate, and dialkyl carbonate, which are recycled into (i) and from any unutilizable product;

(iii) said cracking of said biscarbamate is carried out continuously in the liquid phase, without solvent, in the presence of a catalyst, with the reaction mixture boiling, and with fractionation of the vapors which contain said diisocyanate and said alcohol of the formula $R^2$—OH;

(iv) said diisocyanate and said alcohol obtained in said cracking are fractionally condensed as crude products;

(v) a portion of the cracking reaction mixture containing said by-products is continuously discharged and recycled to said reaction in (i) after reacting with said crude alcohol from (iv); wherein:

$R^1$ is a straight-chain or branched aliphatic hydrocarbon group with a total of 4 to 12 carbon atoms or a substituted or unsubstituted cycloaliphatic hydrocarbon group with a total of 5 to 13 carbon atoms, and $R^2$ is a group obtained by removing the hydroxyl group from a primary aliphatic alcohol with 1 to 8 carbon atoms.

2. The process of claim 1, wherein the amount of said by-products in (i) is 5 to 80 g per 1 mole of said diamine.

3. The process of claim 1, wherein said (cyclo)aliphatic diamine is selected from the group consisting of 1,4-butanediamine, 2-methyl-1,5-pentanediamine, 2-ethyl-1,4-butanediamine, 1,6-hexanediamine, mixtures of 2,2,4- and 2,4,4-trimethyl-1,6-hexanediamine, 1,8-octanediamine, 1,10-decanediamine, 1,12-dodecanediamine, 1,4-cyclohexanediamine, 2-methyl-1,3-cyclohexanediamine, 4-methyl-1,3-cyclohexanediamine, mixtures of 2- and 4-methyl-1,3-cyclohexanediamine, 1,3-cyclohexanebis(methylamine), 1,4-cyclohexanebis(methylamine), mixtures of 1,3- and 1,4-cyclohexanebis(methylamine), 4,4'-methylenebis(cyclohexanamine), 5-amino-1,3,3-trimethylcyclohexanemethylamine and octahydro-4,7-methano-1H-indenebis(methylamine).

4. The process of claim 1, wherein said alcohol is selected from the group consisting of methanol, ethanol, propanol, butanol, isobutanol, pentanol, isopentanols, hexanol, isohexanols, and 2-ethylhexanol.

5. The process of claim 1, wherein the molar ratio of said diamine, said urea, and said alcohol reacted in (i) is 1 : 2.03 : 4.0 to 1 : 2.2 : 10.

6. The process of claim 5, wherein the molar ratio of said diamine, said urea, and said alcohol reacted in (i) is 1 : 2.06 : 7 to 1 : 2.1 : 7.

7. The process of claim 1, wherein the reaction of (i) is carried out at a temperature of 180° to 250° C. and at a pressure of 2 to 80 bar over a period of 3 to 20 hours.

8. The process of claim 7, wherein the reaction of (i) is carried out at a temperature of 220° to 240° C. and at a pressure of 10 to 13 bar over a period of 5 to 8 hours.

9. The process of claim 1, wherein said cracking is carried out at a temperature of 180° to 280° C. and at a pressure of 0.001 to 2 bar.

10. The process of claim 9, wherein said cracking is carried out at a temperature of 230° to 240° C. and at a pressure of 0.005 to 0.05 bar.

11. The process of claim 1, wherein said cracking is carried out in the presence of a catalyst selected from the group consisting of zinc chloride, zinc bromide, zinc iodide, stannous chloride, stannous bromide, and stannous iodide.

12. The process of claim 1, wherein in said cracking the ratio by weight of said discharged portion of said reaction mixture to initial biscarbamate is 1:20 to 1:1.15.

13. The process of claim 12, wherein in said cracking the ratio by weight of said discharged portion of said reaction mixture to initial biscarbamate is 1:8 to 1:3.

14. The process of claim 1, further comprising fractionally distilling said crude diisocyanate to obtain substantially pure diisocyanate.

15. The process of claim 14, wherein the bottoms from said fractionally distilling step are, after reacting with said crude alcohol, recycled to the reaction of (i).

* * * * *